United States Patent [19]

Herweh et al.

[11] 4,348,508
[45] Sep. 7, 1982

[54] 3-SUBSTITUTED-7-ALKOXY-2,2'-SPIROBI[2H-1-BENZOPYRANS]

[75] Inventors: John E. Herweh, Lancaster; Thomas B. Garrett, Lititz; Alan B. Magnusson, Lancaster, all of Pa.

[73] Assignee: Armstrong World Industries, Inc., Lancaster, Pa.

[21] Appl. No.: 277,175

[22] Filed: Jun. 25, 1981

[51] Int. Cl.$^3$ ............... C08F 234/02; C07D 311/96
[52] U.S. Cl. .................................. 526/268; 568/313; 549/344; 430/541
[58] Field of Search ............... 260/345.2; 526/268

[56] References Cited

U.S. PATENT DOCUMENTS

| | | | |
|---|---|---|---|
| 2,978,462 | 4/1961 | Berman et al. | 260/345.2 |
| 3,022,318 | 2/1962 | Berman et al. | 260/345.2 |
| 3,666,525 | 5/1972 | Kimura et al. | 260/345.2 |
| 3,810,762 | 5/1974 | Laridon et al. | 260/345.2 |
| 3,810,763 | 5/1974 | Laridon et al. | 260/345.2 |
| 3,899,514 | 8/1975 | Baumann et al. | 260/345.2 |
| 3,971,808 | 7/1976 | Baumann et al. | 260/345.2 |
| 4,029,677 | 6/1977 | Baumann et al. | 260/345.2 |
| 4,110,348 | 8/1978 | Baumann et al. | 260/345.2 |

FOREIGN PATENT DOCUMENTS 10740  5/1980  European Pat. Off. ......... 260/345.2

OTHER PUBLICATIONS

Feichtmayr et al., Liebigs Ann. Chem., 1979(9), 1337-1345.

Primary Examiner—Nicky Chan

[57] ABSTRACT

Substituted Spirobi[2H-1-benzopyrans] particularly suitable for use as precursors to stable colored pyrylium salts are disclosed.

5 Claims, No Drawings

3-SUBSTITUTED-7-ALKOXY-2,2'-SPIROBI[2H-1-BENZOPYRANS]

This invention relates to spirobipyrans.

More specifically, this invention relates to spirobi[2H-1-benzopyrans].

Spirobipyrans are of interest as precursors for the UV generation of colored pyrylium salts for use in applications as varied as optical data storage to the formation of non-contact decorative patterns (See S. Maslowski, "High Density Data Storage UV Sensitive Tape," Applied Optics, 13, No. 4, 857 (1974).

The present invention provides a novel type of substituted spirobi[2H-1-benzopyran] particularly suitable for use as precursors to stable colored pyrylium salts.

According to this invention there is provided a compound having the formula

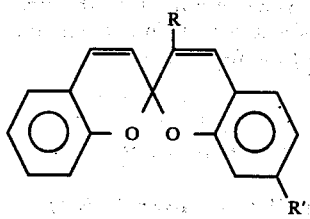

wherein R represents $C_1$–$C_{12}$ alkyl, alkylene aryl, aryl or unsaturated alkyl and R' represents alkoxy.

The term "$C_1$–$C_{12}$ alkyl" is used in the specification and claims to signify a straight or branched alkyl group containing from 1 to 12 carbon atoms, with no more than 6 carbon atoms in its longest chain.

The term "aryl" is used in the specification and claims to signify phenyl or naphthyl, both of which may be unsubstituted or substituted in up to two positions with a substituent selected independently from $C_1$–$C_4$ alkyl, halo or —$NO_2$. "$C_1$–$C_4$ alkyl" is used above to signify a straight or branched alkyl group containing from 1 to 4 carbon atoms and "halo" is used above to signify fluoro, chloro, iodo and bromo.

The term "alkylene aryl" is used in the specification and claims to signify a moiety of the formula M-X-, wherein M represents aryl, as defined above, and X represents a straight or branched alkyl group having from 1 to 3 carbon atoms.

The term "unsaturated alkyl group" is used in the specification and claims to signify a straight or branched alkyl group containing at least 1 carbon—carbon double bond and having from 2 to 12 carbon atoms, with no more than 6 carbon atoms in its longest chain.

The term "alkoxy" is used in the specification and claims to signify a moiety of the formula—OR", wherein R" is a straight or branched alkyl group containing from 1 to 4 carbon atoms.

The novel substituted spirobi[2H-benzopyrans] of this invention are prepared via the straightforward reaction of a styryl ketone and the appropriate 4-alkoxy-2-hydroxybenzaldehyde according to the following reaction formula and as further illustrated in the examples:

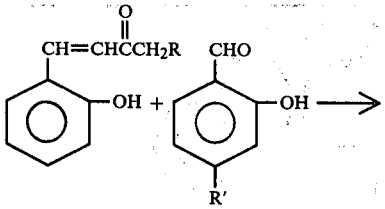

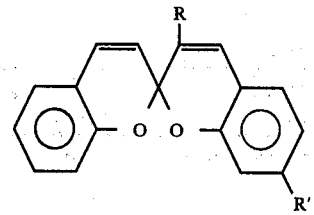

wherein R and R' are as defined above.

The styryl ketones specified above which are not available commercially can be prepared via the reaction of salicylaldehyde and a corresponding ketone according to the following reaction formula:

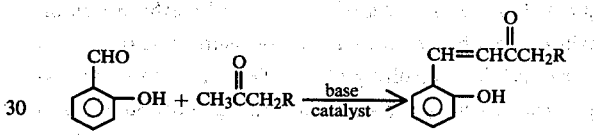

The preparation of such styryl ketones is further documented in the literature: see *Organic Reactions*, vol. 16., J. Wiley and Sons, Inc., N.Y. 1968; E. D. Bergmann, A. Weizmann and E. Fischer, J. Am. Chem. Soc., 72 5009 (1950), D. M. Heilbron; F. Irving, J. Chem. Soc. 936 (1929).

The 4-alkoxy-2-hydroxybenzaldehydes utilized herein can be prepared using the procedure as set forth in Collins et al., J. Chem. Soc. 1950 1876.

The stability of the colored pyrylium salts resulting from interaction of photogenerated protic acids with the spirobipyrans is importanherein can be prepared using the procedure as set forth in Collins et al., J. Chem. Soc. 1950 1876.

The stability of the colored pyrylium salts resulting from interaction of photogenerated protic acids wtion product (2.3 g) was suspended in 50 ml of acetone and the resulting deep red mixture was neutralized with dilute ammonium hydroxide. The deep red color faded to a rust color and a white solid precipitated. The solid precipitate was filtered with suction and washed with fresh acetone. Concentration of the combined washings and main filtrate at reduced pressure on a Rota-vap left a residual gum and water mixture. This mixture was extracted with ether and the combined extracts were dried over anhydrous magnesium sulfate. The dried and filtered ethereal solution was filtered and concentrated under reduced pressure to give an oil, 1.7 g. Upon cooling, and scratching the oil crystallized to a pale green solid, MP 90°–97°. The crude spirobipyran was recrystallized once from benzene-hexane (50/50 by vol.) and then from absolute alcohol to give colorless crystals, MP 100°–102° C. UV ($CH_3CN$) 303 nm ($\epsilon$7940), 293 (9520), 262 (19,400).

The NMR assignments for 3-methyl-7-methoxy-2,2'-spirobi(2H-1-benzopyran) are summarized below:

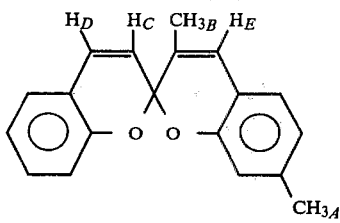

| Proton | $H_A$ | $H_B$ | $H_C$ | $H_D$ & $H_E$ | Aryl Protons |
|---|---|---|---|---|---|
| Chemical shifts,*ppm, | 3.68 (S,3H's) | 1.97 (S,3H's) | 5.94 (d,1H) | in aromatic region | 6.4–7.3 |

*in CDCl$_3$ solvent, TMS as internal standard.

EXAMPLE 3

Copolymerization of Methyl Methacrylate with 3-Allyl-7-Methoxy-2,2'-Spirobi[2H-1-Benzopyran]

Methyl methacrylate (30 g 0.30 mol) and 3-allyl-7-methoxy-2,2'-spirobi[2H-1-benzopyran] (1.5 g, 0.0047 mol) along with 0.09 g of 2,2'-azobis(2-methylpropionitrile) were charged into a glass pressure tube (ca. 70 ml capacity). The resulting clear pale yellow solution was given a sub-surface purge with nitrogen for 30 min and sealed. The air-tight tube was placed in a water bath maintained at 70° C. for 2.5 hrs. After cooling to room temperature, the glass tube was opened and the copolymer (a glass-like rod) was removed.

The copolymer was reprecipitated from ethyl acetate (8.2% solution) by addition to excess hexane and dried in vacuo. UV (copolymer film) 300 nm, 288 and 260.

What is claimed is:

1. A spirobipyran compound having the formula

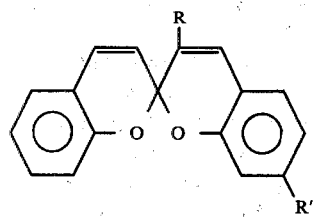

wherein R represents $C_1$–$C_{12}$ alkyl, alkylene aryl, aryl or unsaturated alkyl and R' represents alkoxy.

2. The compound of claim 1 which is 3-allyl-7-methoxy-2,2'-spirobi[2H-1-benzopyran].
3. The compound of claim 1 which is 3-methyl-7-methoxy-2,2'-spirobi[2H-1-benzopyran].
4. A copolymer produced by the free radical polymerization of a spirobipyran compound of claim 1 and an acrylate of the formula

wherein X is H or $CH_3$ and X' is H or a straight or branched alkyl group having from 1 to 12 carbon atoms.

5. The copolymer of claim 4 wherein the spirobypran compound is 3-allyl-7-methoxy-2,2'-spirobi-[2H-1-benzopyran] and the acrylate is methyl methacrylate.

UNITED STATES PATENT AND TRADEMARK OFFICE
CERTIFICATE OF CORRECTION

PATENT NO. : 4,348,508

DATED : September 7, 1982

INVENTOR(S) : John E. Herweh et al

It is certified that error appears in the above-identified patent and that said Letters Patent are hereby corrected as shown below:

Column 2, lines 42-46 should be deleted; line 48, the word "wtion" should be deleted; line 48, following the word "acids", the following should be inserted:

-- with the spirobipyrans is important. It is known that the nature of ring substitution (see rings C and D, below) can influence stability. (G. Arnold, G. Paal, and H. P. Vollmer, Z. Naturforsch. $\underline{B}$ $\underline{25}$ (12), 1413 (1970); U.S. 3,733,197 to C. Schiele.)

Further, it has now been found that substitution at the 7-position of ring D of a $\pi$ electron donating group is effective in stabilizing the color of pyrylium salts. The compounds of this invention have been found to be particularly effective in this respect.

It has also been discovered that the spirobipyrans of this invention may be copolymerized with acrylates via a free radical process initiated by 2,2'-azobis(2-methylpropionitrile). The resulting copolymers are precursors to chromogenic materials that find varied application from optical data storage to the formation of noncontact decorative patterns.

UNITED STATES PATENT AND TRADEMARK OFFICE
CERTIFICATE OF CORRECTION

PATENT NO. : 4,348,508
DATED : September 7, 1982
INVENTOR(S) : John E. Herweh et al It is certified that error appears in the above-identified patent and that said Letters Patent are hereby corrected as shown below:

The term "acrylates" as used herein refers to acrylates and methacrylates that have the formula:

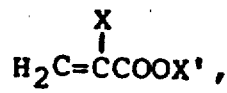

$$H_2C=\overset{X}{\underset{|}{C}}COOX',$$

wherein X is H or $CH_3$ and X' is H or a straight or branched alkyl group having from 1 to 12 carbon atoms.

Reference is now made to the following examples which is provided to illustrate but not to limit the practice of this invention.

Example 1

This example demonstrates the preparation of 3-Allyl-7-Methoxy-2,2'-Spirobi[2H-1-Benzopyran].

Ethereal hydrogen chloride (150 ml, 3.3M) was added to a chilled pale amber ethereal solution (150 ml) of 4-methoxy salicylaldehyde (6.7g, 0.03 mol) and 4-butyl-1-ene-o-hydroxystyryl ketone (4.56g, 0.03 mol). The color deepened to dark red on standing in ice water. After ca. 48 hours at room temperature, the reaction mixture (dark red-purple) was filtered. The reddish brown filter-cake was washed with fresh ether and air-dried.

UNITED STATES PATENT AND TRADEMARK OFFICE
CERTIFICATE OF CORRECTION

PATENT NO. : 4,348,508

DATED : September 7, 1982

INVENTOR(S) : John E. Herweh et al

It is certified that error appears in the above-identified patent and that said Letters Patent are hereby corrected as shown below:

A slurry of the dried filter-cake with acetone was neutralized with dilute ammonium hydroxide, and the resulting mixture was filtered. The filtrate was concentrated under reduced pressure on a Rota-vap, and the residue extracted with ether. The combined dark amber to red ether extract was dried over anhydrous magnesium sulfate. After 16 hours the dried ethereal solution was filtered and concentrated under reduced pressure to dryness, and left a pale amber to brown viscous oil (2.5g). TLC of this viscous oil on alumina 60 $F_{254}$ and on silica gel 60 $F_{254}$ indicated the presence of a single major component. Chromatography of the viscous brown oil (2.5g) on alumina (Fisher A-540) gave 3-allyl-7-methoxy-2,2'-spirobi[2H-1-benzopyran] as a pale amber viscous oil. UV($CH_3CN$): 305 nm ($\epsilon$6774), 292 (8,065), 263 (14731) and 210 (34,624) Elemental analyses for $C_{12}H_{18}O_3$: calcd: C,79.2; H,5.7; found: C,79.2; H,5.8.

UNITED STATES PATENT AND TRADEMARK OFFICE
CERTIFICATE OF CORRECTION

PATENT NO. : 4,348,508
DATED : September 7, 1982
INVENTOR(S) : John E. Herweh et al It is certified that error appears in the above-identified patent and that said Letters Patent are hereby corrected as shown below:

The NMR assignments are summarized below:

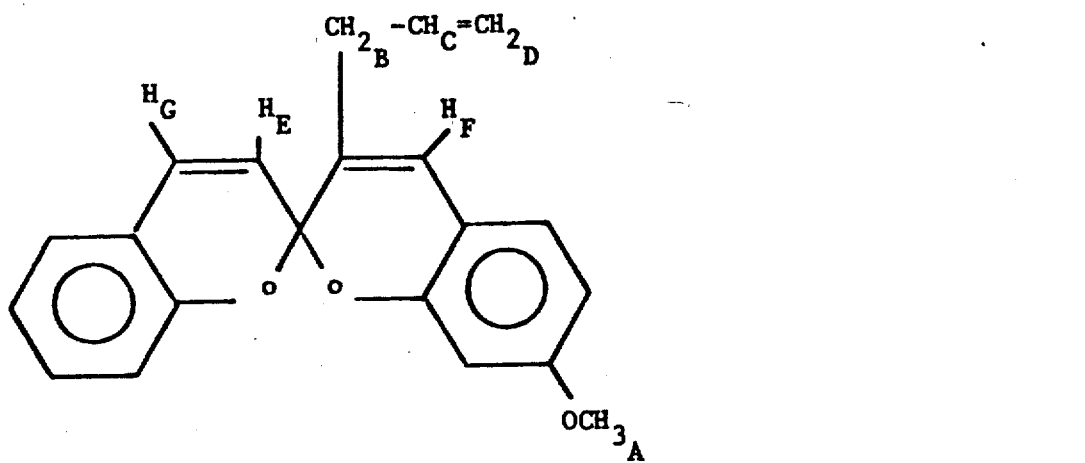

| Proton | $H_A$ | $H_B$ | $H_C$ | $H_D$ |
|---|---|---|---|---|
| Chemical* shifts, ppm | 3.60(s) | 2.96(d) | 5.9(m) | 5.1(d) |

UNITED STATES PATENT AND TRADEMARK OFFICE
CERTIFICATE OF CORRECTION

PATENT NO. : 4,348,508

DATED : September 7, 1982

INVENTOR(S) : John E. Herweh et al

It is certified that error appears in the above-identified patent and that said Letters Patent are hereby corrected as shown below:

| Proton | $H_E$ | $H_F$ and $H_G$ | Aryl Protons |
|---|---|---|---|
| Chemical* shifts, ppm | 5.94(d) | In Aromatic Region | 6.3-7.3 |

*in $CDCl_3$ solvent, TMS as internal standard.

Example 2

Preparation of 3-methyl-7-methoxy-2,2'spirobi-(2H-1-benzopyran).

To a solution of 2-hydroxy styryl ethyl ketone (1.76 g, 0.01 mol) and 4-methoxy-2-hydroxybenzaldehyde (1.52 g, 0.01 (mol) in 20 ml of glacial acetic acid was added with cooling 50 ml of glacial acetic acid

UNITED STATES PATENT AND TRADEMARK OFFICE
CERTIFICATE OF CORRECTION

PATENT NO. : 4,348,508
DATED : September 7, 1982
INVENTOR(S) : John E. Herweh et al It is certified that error appears in the above-identified patent and that said Letters Patent are hereby corrected as shown below:

containing ca. 4 g of anhydrous hydrogen chloride. The reaction mixture turned orange initially, then red and after ca. 24 hrs. at room temperature became deep magenta. The reaction mixture was filtered with suction and the filter-cake was washed with ether and air-dried to give 2.3 g of a red to burgundy colored powder – presumably the pyrylium salt.

The crude reaction —

Signed and Sealed this

Fifteenth Day of February 1983

[SEAL]

Attest:

GERALD J. MOSSINGHOFF

Attesting Officer

Commissioner of Patents and Trademarks